United States Patent [19]
Bertocchio et al.

[11] Patent Number: 5,917,098
[45] Date of Patent: Jun. 29, 1999

[54] PREPARATION OF 1,1,1,3,3-PENTACHLOROBUTANE AND 1,1,1,3,3-PENTAFLUOROBUTANE

[75] Inventors: Rene Bertocchio, Vourles Par Vernaison; Andre Lantz, Domaine de la Hetraie; Laurent Wendlinger, Saint Genis Laval, all of France

[73] Assignee: Elf Atochem S.A., France

[21] Appl. No.: 08/790,757

[22] Filed: Jan. 27, 1997

[30] Foreign Application Priority Data

Feb. 1, 1996 [FR] France .................................. 96 01214

[51] Int. Cl.$^6$ .................................................. C07C 17/02
[52] U.S. Cl. ........................... 570/164; 570/166; 570/193
[58] Field of Search .................... 570/164, 172, 570/193, 166

[56] References Cited

U.S. PATENT DOCUMENTS

| | | | |
|---|---|---|---|
| 2,543,648 | 3/1951 | Strosacker et al. | 570/167 |
| 3,862,978 | 1/1975 | Decker et al. | 570/172 |
| 5,395,997 | 3/1995 | Van Der Puy et al. | 570/167 |

FOREIGN PATENT DOCUMENTS

| | | |
|---|---|---|
| 699649 | 3/1996 | European Pat. Off. . |
| 2213257 | 8/1974 | France . |
| 9504021 | 2/1995 | WIPO . |

OTHER PUBLICATIONS

Ind. Eng. Chem. 39, pp. 418–420, 1947.

Izv. Akad. Nauk SSSR (6), pp. 1333–1336, 1980; translation/reprint by Plenum Publishing Corporation, pp. 952–955, 1980.

Izv. Akad. Nauk SSSR (8), pp. 1903–1905, 1979; translation/reprint by Plenum Publishing Corporation, pp. 1766–1769, 1980.

Zhur. Org. Khim 24 (7), p. 1558, 1988; translation/reprint by Plenum Publishing Corporation, p. 1404, 1988; with Chemical Abstract of above, Organofluorine Chemistry, Issue 10, 110:172651u, 1989.

Kotora et al., React. Kinet. Catal. Lett., vol. 44 (2), pp. 415–419, 1991.

Kotora, et al., "Addition of tetrachloromethane to halogenated ethenes catalyzed by transition metal complexes." *Journal of Molecular Catalysis,* (1992) 77:51–60.

French Search Report, dated Oct. 17, 1996.

Journal of the American Chemical Society, vol. 67, pp. 1194–1197 and 1197–1199, 1945.

Journal of the American Chemical Society, vol. 80, pp. 1711–1713, 1958.

CA 115:182556, Kotora et al., 1991.

*Primary Examiner*—Jane Fan
*Attorney, Agent, or Firm*—Bell, Boyd & LLoyd

[57] ABSTRACT

1,1,1,3,3-Pentachlorobutane, whose fluorination leads to 1,1,1,3,3-pentafluorobutane, is prepared with high yield and selectivity by addition of carbon tetrachloride to 2-chloropropene in the presence of a copper salt and an amine.

24 Claims, No Drawings

PREPARATION OF 1,1,1,3,3-PENTACHLOROBUTANE AND 1,1,1,3,3-PENTAFLUOROBUTANE

FIELD OF THE INVENTION

The present invention relates to the field of halogen-containing hydrocarbons and more particularly to the preparation of 1,1,1,3,3-pentachlorobutane and to its fluorination to 1,1,1,3,3-pentafluorobutane.

BACKGROUND OF THE INVENTION

With a boiling point of 40° C., 1,1,1,3,3-pentafluorobutane (known under the name F365 mfc) is a potential substitute for liquid chlorofluoroalkanes which are banned by the Montreal Protocol, most particularly fluorotrichloromethane (F11; b.p.=27° C.) and trichlorotrifluoroethane (F113; b.p.=47° C.).

Processes allowing F365 mfc to be prepared are few in number and generally involve the fluorination of a chloro precursor such as 2,2-difluoro-4,4,4-trichlorobutane, 2-bromo-2,4,4,4-tetrachlorobutane or 1,1,1,3,3-pentachlorobutane.

Henne et al. (J. Am. Chem. Soc. 67, p. 1194–1197 and 1197–1199, 1945) chlorinate 2,2-difluorobutane to obtain, with a selectivity of 52.5%, 2,2-difluoro-4,4,4-trichlorobutane (F362 jfc) which is then fluorinated to F365 mfc. McBee and Hausch (Ind. Eng. Chem. 39, p. 418–420, 1947) fluorinate F362 jfc with HF/HgO or with the mixture $SbF_3/SbCl_5$, but the fluorination yields do not exceed 15%. All these processes are characterized by low yields, essentially due to the lack of selectivity of the chlorination reactions leading to the chloro precursor.

Another method for the preparation of F365 mfc, described by Tarrant et al. (J. Am. Chem. Soc. 80, p.1711–1713, 1958), consists of the radical addition of $CCl_3Br$ to 2-chloropropene and fluorination with HF, in the absence of catalyst, of the 1:1 addition product ($CCl_3CH_2CBrClCH_3$) obtained, in a yield of 34%. This method does not improve the overall yield since, in this case, a lack of selectivity is observed due to the formation of telomers promoted by the radical initiation with benzoyl peroxide.

Another chloro precursor of F365 mfc is 1,1,1,3,3-pentachlorobutane which, according to Friedlina et al. [Izv Akad. Nauk SSSR (6), p. 1333–1336 (1980) and (8), p. 1903-5 (1979)], may be obtained by telomerization of vinylidene chloride with 1,1,1-trichloroethane or that of 2-chloropropene with $CCl_4$ in the presence of iron pentacarbonyl. In both cases, a mixture of three telomers is obtained and the selectivity towards 1,1,1,3,3-pentachlorobutane (1:1 addition product) is insufficient to be of any definite economic value.

The direct preparation of F365 mfc according to the method of Bloshchitsa et al. (Zhur. Org. Khim 24(7), p. 1558, 1988) by the action of hydrofluoric acid and sulphur tetrafluoride on diketene constitutes, in point of fact, the only method leading to F365 mfc with an acceptable yield (70%). Unfortunately, this process uses two relatively uncommon starting materials, diketene and sulphur tetrafluoride.

F365 mfc is also a by-product in the manufacture of 1,1-dichloro-1-fluoroethane (F141b), but the similarity of their boiling points (F141b : b.p.=32° C.; F365 mfc : b.p.=40° C.) and the existence of a minimum-boiling-point azeotropic mixture do not allow ready separation of the two products. A separation process, based on the principle of distillation in the presence of an excess of HF, is however described in patent EP 395,793.

Amine/cuprous salt complexes are known catalysts for the addition of polyhalo compounds to olefins (Kotora et al., J. of Molecular Catalysis 77, p. 51–61, 1992), but these authors show that the yield of 1:1 addition product may pass from 97% for vinyl chloride to 11% for 1,2-dichloroethylene.

DESCRITION OF THE INVENTION

While investigating a process allowing F365 mfc to be prepared in high yield and selectivity, it has now been found that 2-chloropropene is classed among the olefins which are reactive towards carbon tetrachloride and may, under certain conditions, lead to the expected 1:1 addition product, 1,1,1,3,3-pentachlorobutane, in excellent yield and with an excellent selectivity, the formation of by-products, telomers or elimination products being negligible. Furthermore, among these by-products, the $C_4H_4Cl_4$ olefins which may be formed by dehydrochlorination of 1,1,1,3,3-pentachlorobutane are readily fluorinated to 1,1,1,3,3-pentafluorobutane.

The first subject of the invention is thus a process for the preparation of 1,1,1,3,3-pentachlorobutane by addition of carbon tetrachloride to 2-chloropropene, characterized in that the process is performed in the presence of a copper salt and an amine.

The subject of the invention is also a process for the preparation of F365 mfc, comprising a first step of addition of carbon tetrachloride to 2-chloropropene and a step of fluorination with hydrofluoric acid of the 1,1,1,3,3-pentachlorobutane thus obtained.

A cuprous salt, preferably a halide and more particularly cuprous chloride, is advantageously used as copper salt.

The amine to be used may be a mono-, di- or trialkylamine whose linear or branched alkyl radical(s) may contain from 1 to 8 (preferably 2 to 4) carbon atoms. A cyclanic amine, for example cyclohexylamine, may also be used. A primary amine, and more particularly isopropylamine, is advantageously used.

The 2-chloropropene may be obtained in a manner which is known per se, by dehydrochlorination of 1,2-dichloropropane or of 2,2-dichloropropane (thermally or by the action of glycolic potassium hydroxide) or, preferably, by the action of phenylchloroform on acetone in the presence of a Lewis acid such as zinc chloride or ferric chloride (patent FR 2,213,257); in this case, the yield of 2-chloropropene reaches 77% and the main by-product of the reaction, 2,2-dichloropropane, may readily be converted into 2-chloropropene by elimination of HCl according to the process with glycolic sodium hydroxide or potassium hydroxide described in U.S. Pat. No. 2,543,648.

The $CCl_4/CH_3CCl=CH_2$ molar ratio may range from 2 to 6 but is preferably between 2.5 and 4.5.

The copper salt, in particular the cuprous chloride, has the role of initiating the formation of the trichloromethyl radical and of ensuring transfer of the chlorine to the $CCl_3CH_2CClCH_3$ radical resulting from the addition of the $CCl_3$ radical to 2-chloropropene. It is generally used in an amount such that the molar ratio: copper salt/2-chloropropene is between 0.001 and 0.05, preferably between 0.005 and 0.02.

The amine concentration has a dominant influence on the yield of 1,1,1,3,3-pentachlorobutane. Relative to the total number of moles of the initial reaction mixture ($CCl_4$+$CH_3CCl=CH_2$+CuCl+amine), it may range from 0.5 to 10%, but is preferably between 1 and 8% and, more particularly, between 2.5 and 6%.

The reaction may be carried out at a temperature of between 80 and 130° C., but is preferably carried out at between 90 and 110° C.

The 1,1,1,3,3-pentachlorobutane formed, which may be separated from the reaction mixture by processes that are known per se, in particular by filtration, acidic washing, washing with water, drying and distillation, is used in accordance with the second aspect of the present invention for the synthesis of 1,1,1,3,3-pentafluorobutane by fluorination using hydrofluoric acid.

This operation may be performed in the liquid phase, in the presence or absence of catalysts. It is generally carried out under autogenous pressure at a temperature of between 80 and 120° C., preferably at about 100° C. The HF/$CCl_3CH_2CCl_2CH_3$ molar ratio may range from 15 to 30, but is advantageously between 20 and 25. Any liquid-phase fluorination catalyst may be used as catalyst, in particular an antimony-based catalyst. However, the best results have been obtained without catalyst.

EXAMPLES

The examples which follow illustrate the invention without limiting it.

Example 1

8 mg of cuprous chloride, 117 mg of n-butylamine, 370 mg of 2-chloropropene (destabilized beforehand by distillation) and, lastly, 3.2 g of carbon tetrachloride were successively introduced into a thick-walled Pyrex tube maintained at 0° C. The tube was then sealed, homogenized and heated at constant temperature (100° C.) for 4 hours with stirring.

After cooling, the tube was opened on a gas manifold, allowing the gas phase to be recovered quantitatively, the liquid phase being transferred into a flask for separate analysis. The two phases were analysed by gas chromatography and the reaction balance was reconstituted from these analyses.

The results of this test (Test 1-a), as well as the operating conditions and the results obtained with other amines (Tests 1-b to 1-g), are summarized in Table (I), in which the abbreviations have the following meanings:

DC: degree of conversion 360 jfa: 1,1,1,3,3-pentachlorobutane

TABLE 1

| | Test No. | | | | | | |
|---|---|---|---|---|---|---|---|
| Amine | 1-a n-butyl-amine | 1-b isopropyl-amine | 1-c tert-butyl-amine | 1-d comparative ethanol-amine | 1-e diethyl-amine | 1-f triethyl-amine | 1-g cyclo-hexyl-amine |
| Operating conditions: | | | | | | | |
| amine concentration (mol %) | 5.9 | 5 | 3.35 | 1.24 | 4 | 4.7 | 6 |
| $CCl_4$/2-chloropropene molar ratio | 4.3 | 4 | 4 | 4 | 4 | 4.1 | 3.9 |
| CuCl/2-chloropropene molar ratio | 0.017 | 0.014 | 0.014 | 0.01 | 0.02 | 0.02 | 0.016 |
| Results: | | | | | | | |
| DC (%) of the 2-chloropropene | 99.7 | 98.4 | 99.3 | 2.7 | 84.3 | 57.1 | 95.4 |
| Selectivity (%) towards: | | | | | | | |
| 360 jfa | 90.7 | 94.2 | 85.7 | 0.8 | 68 | 37.1 | 90.3 |
| olefins | 1.8 | 0.3 | 3.8 | 0.4 | 0.2 | 1 | 1.3 |
| heavy fractions | 7.2 | 3.8 | 9.9 | 1.6 | 16.1 | 19 | 9.4 |
| DC (%) of $CCl_4$ into $CHCl_3$ | 1.8 | 1 | 0.3 | 1 | 0.7 | 0.7 | 1.1 |

Example 2

The process was carried out as in Example 1 with isopropylamine, but varying its concentration in the reaction mixture.

The results are collated in Table II below.

TABLE II

| | Test No. | | | | | |
|---|---|---|---|---|---|---|
| | 2-a | 2-b | 2-c(*) | 1-b | 2-d(**) | 2-e |
| Operating conditions: | | | | | | |
| isopropyl-amine concentration (mol %) | 0.5 | 1.0 | 2.6 | 5.0 | 6.9 | 7.5 |
| $CCl_4$/2-chloropropene molar ratio | 4.4 | 4.2 | 4.1 | 4.0 | 4.1 | 3.9 |

TABLE II-continued

| | Test No. | | | | | |
|---|---|---|---|---|---|---|
| | 2-a | 2-b | 2-c(*) | 1-b | 2-d(**) | 2-e |
| CuCl/2-chloropropene molar ratio | 0.0136 | 0.0094 | 0.0197 | 0.014 | 0.0310 | 0.0130 |
| Results: | | | | | | |
| DC (%) of the 2-chloropropene | 1 | 54 | 97.8 | 98.4 | 79.3 | 57.4 |
| Selectivity (%) towards: | | | | | | |
| 360 jfa | 1 | 53.6 | 93.5 | 94.2 | 69.1 | 34 |
| olefins | 0 | 0 | 0.4 | 0.3 | 3.6 | 6.4 |
| heavy fractions | 0 | 0.4 | 4.0 | 3.8 | 6.4 | 17.2 |
| DC (%) of the $CCl_4$ into $CHCl_3$ | 0.2 | 0.5 | 0.6 | 1.0 | 2.1 | 1.3 |

(*): 6 hours at 100° C. instead of 4 hours at 100° C.
(**): 2 hours at 100° C. instead of 4 hours at 100° C.

Example 3

1 g (0.01 mol) of cuprous chloride and 4.60 g (0.077 mol) of isopropylamine were successively introduced into a 500 ml three-necked round-bottomed flask equipped with a condenser at −25° C. and a dropping funnel, followed, after stirring, by 180.5 g of $CCl_4$ (1.17 mol). 29.6 g (0.38 mol) of 2-chloropropene were then introduced into the bright-blue solution and the reaction medium was heated at 100° C. for two hours and thirty minutes.

After stopping the heating and cooling for 6 hours, the reaction mixture was filtered through "Decalite" until the blue-green colour disappeared, then washed twice with 1N hydrochloric acid to remove the traces of unreacted amine. The organic phase was then washed with water until neutral and dried over sodium sulphate. The 1,1,1,3,3-pentachlorobutane was then separated from the excess $CCl_4$ by distillation under vacuum between room temperature and 50° C.

Along with 1.4 g of unreacted 2-chloropropene (DC= 95.3%), 79 g of 1,1,1,3,3-pentachlorobutane, 1.7 g of $C_4Cl_4H_4$ olefin and 2.7 g of heavy telomers including 90% of dimer were obtained. The purity of the 360 jfa thus obtained by distillation reaches 98% and the degree of conversion of the 2-chloropropene into 360 jfa is 88.6%; if it is considered that the olefin becomes fluorinated into F365 mfc in the same manner as 360 jfa, the overall yield reaches 90.8% under these conditions. Example 4

41.1 g of 1,1,1,3,3-pentachlorobutane (0.178 mol) and 82.2 g of anhydrous hydrofluoric acid (4.108 mol) were successively introduced into an 800 ml 316L stainless steel autoclave equipped with a pressure indicator, a thermometer probe, a cracking disc and a system for stirring with a magnetic stirrer-bar.

With the reactor heated to 100° C., the pressure gradually rose to reach 30.4 bar. After 8 hours the reaction system was cooled to room temperature and a residual pressure of 12.8 bar was observed.

The light organic compounds (23.2 g) and the hydracids (96.8 g) were removed by degassing and then flushing with helium. The heavy products (2 g) were collected after opening the autoclave.

Analysis of the various phases collected allowed a degree of conversion of the 1,1,1,3,3-pentachlorobutane and a selectivity towards 1,1,1,3,3-pentafluorobutane to be calculated, these respectively reaching 98.1% and 61%.

The other reaction products were mainly underfluorinated compounds: $C_4H_5ClF_4$ (selectivity=14.8%), $C_4H_5Cl_2F_3$ (2 isomers: selectivity=17.8%) and $C_4H_5Cl_3F_2$ (selectivity=1%). These compounds may advantageously be recycled into the reactor in order to be converted into 1,1,1,3,3-pentafluorobutane.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process comprising preparation of 1,1,1,3,3-pentachlorobutane by addition of carbon tetrachloride to 2-chloropropene, performed in the presence of a copper salt and an amine, the amine is a primary, secondary, tertiary amine or cyclohexylamine containing from 1 to 8 carbon atoms, and the molar concentration of amine is between 1 and 10% relative to the total number of moles of initial reaction mixture.

2. Process according to claim 1, wherein the copper salt is cuprous chloride.

3. Process according to claim 1 wherein the amine is isopropylamine.

4. Process according to claim 1, wherein the $CC_4$/$CH_3CCl=CH_2$ molar ratio is between 2 and 6.

5. Process according to 1, wherein the molar ratio: copper salt/2-chloropropene is between 0.001 and 0.05.

6. Process according to claim 1, wherein the process is performed at a temperature of between 80 and 130° C.

7. Process according to claim 1, wherein the primary alkylamine contains 2 to 4 carbon atoms.

8. Process according to claim 4, wherein the molar ratio is between 2.5 and 4.5.

9. Process according to claim 5, wherein the molar ratio is between 0.005 and 0.02.

10. Process according to claim 1, wherein the molar concentration is between 1 and 8%.

11. Process according to claim 10, wherein the molar ratio is between 2.5 and 6%.

12. Process according to claim 6, wherein the temperature is between 90 and 110° C.

13. Process for preparation of 1,1,1,3,3-pentachlorobutane comprising addition of carbon tetrachloride to 2-chloropropene performed in the presence of cuprous chloride and isopropylamine, the molar ratio of $CCl_4$/$CH_3CCl=CH_2$ is between 2.5 and 4.5, the molar ratio of cuprous chloride/2-chloropropene is between 0.005 and 0.02, and the molar concentration of amine is between 2.5 and 6% relative to the total number of moles of initial reaction mixture.

14. Process comprising preparation of 1,1,1,3,3-pentachlorobutane by addition of carbon tetrachloride to 2-chloropropene, performed in the presence of a copper salt and an amine, the amine is a primary amine containing from 2 to 4 carbon atoms, and the molar concentration of amine is between 2.5 and 6% relative to the total number of moles of initial reaction mixture.

15. Process comprising preparation of 1,1,1,3,3-pentachlorobutane by addition of carbon tetrachloride to 2-chloropropene, performed in the presence of a copper salt and an amine, the amine is a primary or secondary amine containing from 1 to 8 carbon atoms, and the molar concentration of amine is between 1 and 8% relative to the total number of moles of initial reaction mixture.

16. Process comprising preparation of 1,1,1,3,3-pentachlorobutane by addition of carbon tetrachloride to 2-chloropropene, performed in the presence of a copper salt and an amine, the amine is a primary or secondary amine containing from 1 to 8 carbon atoms, and the molar concentration of amine is between 2.5 and 6% relative to the total number of moles of initial reaction mixture.

17. Process according to claim 15, wherein the amine is primary amine.

18. Process according to claim 15, wherein the amine has 1 to 8 carbon atoms.

19. Process according to claim 15, wherein the amine has 2 to 4 carbon atoms.

20. Process for the preparation of 1,1,1,3,3-pentafluorobutane according to claim 1, comprising a 1,1,1,3,3-pentachlorobutane, obtained by addition of carbon tetrachloride to 2-chloropropene performed in the presence of a copper salt and an amine, being subjected to fluorination with hydrofluoric acid.

21. Process according to claim 20, wherein the fluorination is carried out in the liquid phase at a temperature ranging approximately from 80 to 120° C.

22. Process according to claim 20, wherein the $HF/CCl_3CH_2CCl_2CH_3$ molar ratio is between 15 and 30.

23. Process according to claim 21, wherein the temperature is about 100° C.

24. Process according to claim 22, wherein the molar ratio is between 20 and 25.

* * * * *